United States Patent
Dechow

(10) Patent No.: US 7,776,349 B2
(45) Date of Patent: *Aug. 17, 2010

(54) ORGANO-GEL FORMULATIONS FOR THERAPEUTIC APPLICATIONS

(75) Inventor: Frederick J. Dechow, Shoreline, WA (US)

(73) Assignee: MediQuest Therapeutics, Inc., Bothell, WA (US)

( * ) Notice: Subject to any disclaimer, the term of this patent is extended or adjusted under 35 U.S.C. 154(b) by 1074 days.

This patent is subject to a terminal disclaimer.

(21) Appl. No.: 11/246,296

(22) Filed: Oct. 11, 2005

(65) Prior Publication Data

US 2006/0110342 A1    May 25, 2006

Related U.S. Application Data

(63) Continuation-in-part of application No. 11/150,254, filed on Jun. 13, 2005, which is a continuation-in-part of application No. 11/066,485, filed on Feb. 28, 2005, which is a continuation-in-part of application No. 10/960,516, filed on Oct. 8, 2004.

(51) Int. Cl.
*A61K 9/107* (2006.01)
*A61K 8/06* (2006.01)

(52) U.S. Cl. ..................................... 424/401

(58) Field of Classification Search ........................ None
See application file for complete search history.

(56) References Cited

U.S. PATENT DOCUMENTS

| | | | |
|---|---|---|---|
| 3,883,545 A | 5/1975 | Lohaus et al. | |
| 3,957,971 A | 5/1976 | Oleniacz | |
| 4,021,573 A | 5/1977 | Lee | |
| 4,036,970 A | 7/1977 | Walker et al. | |
| 4,567,161 A | 1/1986 | Posanski et al. | |
| 4,684,661 A | 8/1987 | Stuetz et al. | |
| 4,751,245 A | 6/1988 | Bisacchi et al. | |
| 4,755,534 A | 7/1988 | Stuetz et al. | |
| 4,764,381 A | 8/1988 | Bodor et al. | |
| 4,788,061 A | 11/1988 | Shore | |
| 4,895,727 A | 1/1990 | Allen | |
| 4,920,112 A | 4/1990 | Onishi et al. | |
| 4,940,586 A | 7/1990 | Cheng et al. | |
| 4,957,730 A | 9/1990 | Bohn et al. | |
| 5,030,625 A | 7/1991 | Stuetz et al. | |
| 5,045,317 A | 9/1991 | Chess et al. | |
| 5,051,260 A | 9/1991 | Chess et al. | |
| 5,132,459 A | 7/1992 | Stuetz et al. | |
| 5,181,914 A | 1/1993 | Zook | |
| 5,219,877 A | 6/1993 | Shah et al. | |
| 5,231,183 A | 7/1993 | Nakagawa et al. | |
| 5,264,206 A | 11/1993 | Bohn et al. | |
| 5,296,612 A | 3/1994 | Nakagawa et al. | |
| 5,318,960 A | 6/1994 | Toppo | |
| 5,356,633 A | 10/1994 | Woodle et al. | |
| 5,385,911 A | 1/1995 | Sunkara et al. | |
| 5,401,742 A | 3/1995 | Hirano et al. | |
| 5,514,698 A | 5/1996 | Ahmad et al. | |
| 5,525,635 A | 6/1996 | Moberg et al. | |
| 5,591,774 A | 1/1997 | Yu et al. | |
| 5,639,740 A | 6/1997 | Crandall | |
| 5,652,256 A | 7/1997 | Knowles | |
| 5,654,337 A * | 8/1997 | Roentsch et al. | ............ 514/570 |
| 5,681,849 A | 10/1997 | Richter et al. | |
| 5,693,676 A | 12/1997 | Gorfine | |
| 5,698,589 A | 12/1997 | Allen | |
| 5,741,513 A | 4/1998 | Ghyczy et al. | |
| 5,750,141 A * | 5/1998 | Roberts et al. | ............... 424/449 |
| 5,753,256 A | 5/1998 | Cordes et al. | |
| 5,807,957 A * | 9/1998 | Samour et al. | ................. 528/49 |
| 5,814,305 A | 9/1998 | Laugier et al. | |
| 5,817,875 A | 10/1998 | Karimian et al. | |
| 5,840,283 A | 11/1998 | Sorenson et al. | |
| 5,856,355 A | 1/1999 | Richter et al. | |
| 5,889,039 A | 3/1999 | Knowles | |
| 5,925,669 A | 7/1999 | Katz et al. | |
| 5,935,577 A | 8/1999 | Weiner et al. | |
| 5,945,409 A | 8/1999 | Crandall | |

(Continued)

FOREIGN PATENT DOCUMENTS

| | | |
|---|---|---|
| AU | 642412 | 11/1990 |
| WO | WO-89/00077 | 1/1989 |
| WO | WO-91/11993 A1 | 8/1991 |
| WO | WO-02/34235 | 5/2002 |
| WO | WO-03/020250 | 3/2003 |
| WO | WO-2004/021968 | 3/2004 |
| GB | 2098865 | 12/1982 |
| GB | 2197194 | 5/1988 |

OTHER PUBLICATIONS

"Colloid Science Organogels from water-in-oil microemulsions" Luisi et al., *Colloid & Polymer Science* vol. 268, No. 4, pp. 356-374, 1990.

"Organogels from Lecithins" Scartazzini et al., *J. Phys. Chem.* vol. 92, 1988, pp. 829-833.

"Lecithin Organogel as Matrix for Transdermal Transport of Drugs" Willimann et al., *Journal of Pharmaceutical Sciences*, vol. 81, No. 9, Sep. 1992, pp. 871-874.

"Preparation and characterization of reverse micelle based organogels of piroxicam" Agrawal et al., *Pharmazie* 59 (2004) 3, pp. 191-193.

*Primary Examiner*—Frederick Krass
*Assistant Examiner*—Brian Gulledge
(74) *Attorney, Agent, or Firm*—Connolly Bove Lodge & Hutz LLP

(57) ABSTRACT

A composition suitable for the local delivery of cosmetic and/or pharmaceutical agents into the skin containing at least two biocompatible organic solvents, a polar lipid, a surfactant, water, urea and a thickener wherein the organic solvents include an ester and a dihydric and/or polyhydric alcohol is provided. Also disclosed are compositions that further contain a cosmetic and/or pharmaceutical agent, along with the preparation and use thereof.

34 Claims, No Drawings

U.S. PATENT DOCUMENTS

| | | |
|---|---|---|
| 5,952,499 A | 9/1999 | Whittaker et al. |
| 5,985,860 A | 11/1999 | Toppo |
| 5,985,906 A | 11/1999 | Meingassner et al. |
| 5,993,790 A | 11/1999 | Strauss |
| 6,005,001 A | 12/1999 | Richter et al. |
| 6,017,920 A | 1/2000 | Kamishita et al. |
| 6,042,845 A * | 3/2000 | Sun et al. .................. 424/446 |
| 6,121,314 A | 9/2000 | Richter et al. |
| 6,143,793 A | 11/2000 | Laugier et al. |
| 6,143,794 A | 11/2000 | Chaudhuri et al. |
| 6,159,977 A | 12/2000 | Reeves |
| 6,165,975 A | 12/2000 | Adams et al. |
| 6,172,261 B1 | 1/2001 | Vermeulin et al. |
| 6,231,889 B1 | 5/2001 | Richardson et al. |
| 6,248,363 B1 | 6/2001 | Patel et al. |
| 6,281,239 B1 | 8/2001 | Glassman |
| 6,287,601 B1 | 9/2001 | Russell |
| 6,309,663 B1 | 10/2001 | Patel et al. |
| 6,316,428 B1 * | 11/2001 | Crandall .................. 514/78 |
| 6,380,236 B2 | 4/2002 | Glassman |
| 6,423,683 B1 | 7/2002 | Heaton et al. |
| 6,455,592 B1 | 9/2002 | Laugier et al. |
| 6,485,740 B1 | 11/2002 | Tominaga et al. |
| 6,538,017 B2 | 3/2003 | Greco et al. |
| 6,558,695 B2 * | 5/2003 | Luo et al. .................. 424/449 |
| 6,596,287 B2 | 7/2003 | Deckers et al. |
| 6,610,652 B2 | 8/2003 | Adams et al. |
| 6,632,843 B1 | 10/2003 | Friedman |
| 6,638,981 B2 * | 10/2003 | Williams et al. ............ 514/656 |
| 6,673,842 B2 | 1/2004 | Bhagwat et al. |
| 6,720,001 B2 | 4/2004 | Chen et al. |
| 6,743,417 B2 | 6/2004 | Glassman et al. |
| 6,846,837 B2 | 1/2005 | Maibach et al. |
| 2001/0049386 A1 | 12/2001 | Glassman |
| 2001/0056071 A1 | 12/2001 | Pelliccia et al. |
| 2003/0086881 A1 | 5/2003 | Bohn et al. |
| 2003/0091540 A1 | 5/2003 | Ahmad et al. |
| 2003/0181525 A1 | 9/2003 | Bhagwat et al. |
| 2003/0181526 A1 | 9/2003 | Bhagwat et al. |
| 2003/0185824 A1 * | 10/2003 | Vaishnaw et al. ......... 424/144.1 |
| 2003/0235541 A1 | 12/2003 | Maibach et al. |
| 2004/0039030 A1 | 2/2004 | Bohn et al. |
| 2004/0058954 A1 * | 3/2004 | Burns et al. .................. 514/317 |
| 2004/0062733 A1 | 4/2004 | Birnbaum |
| 2004/0081684 A1 | 4/2004 | Chew et al. |
| 2004/0096410 A1 | 5/2004 | Maley et al. |
| 2004/0101538 A1 | 5/2004 | Larnier et al. |
| 2004/0146470 A1 | 7/2004 | Glassman et al. |
| 2004/0167079 A1 * | 8/2004 | Tidmarsh .................... 514/23 |
| 2004/0197280 A1 | 10/2004 | Repka |
| 2005/0014729 A1 | 1/2005 | Pulaski |
| 2005/0074414 A1 | 4/2005 | Tamarkin et al. |
| 2006/0078577 A1 | 4/2006 | Dechow |
| 2006/0078579 A1 | 4/2006 | Dechow |
| 2006/0078580 A1 | 4/2006 | Dechow |

* cited by examiner

ORGANO-GEL FORMULATIONS FOR THERAPEUTIC APPLICATIONS

CROSS-REFERENCE TO RELATED APPLICATIONS

This application is a continuation-in-part of my copending U.S. application Ser. No. 11/150,254, filed Jun. 13, 2005, entitled ORGANO-GEL FORMULATIONS FOR THERAPEUTIC APPLICATIONS, which in turn is a continuation-in part of my copending U.S. application Ser. No. 11/066,485, filed Feb. 28, 2005, entitled ORGANO-GEL FORMULATIONS FOR THERAPEUTIC APPLICATIONS, which in turn is a continuation-in-part of my copending U.S. application Ser. No. 10/960,516, filed Oct. 8, 2004, entitled ORGANO-GEL FORMULATIONS FOR THERAPEUTIC APPLICATIONS, entire disclosures of which are being incorporated herein by reference.

TECHNICAL FIELD

This disclosure relates to a composition useful in the local delivery of cosmetic and/or pharmaceutical agents into the skin and nails. This composition allows the formulation with the agent(s) to be rapidly absorbed through the skin, to pass through nails, and also to have a pleasing, non-greasy, non-oily appearance and feel.

BACKGROUND

The skin is the largest organ in the body and serves important functions that are necessary to life. The skin acts as a barrier to the invasion of various pathogens and toxic substances. Skin is composed of the two layers: the epidermis is the first layer; and the dermis is the layer below the epidermis.

However, because it must serve as a barrier to the ingress of pathogens and toxic materials, and the egress of physiologic fluids, the skin is highly impermeable. It must be impermeable to preserve its own integrity while at the same time maintaining the delicate dynamic electrolyte balance of the body. The skin must serve a containment function; it must also function as a microbial, chemical, radiation and thermal barrier.

A good deal of this impermeability of the skin results from the nature of one very thin layer created by normal developmental and physiological changes in the skin. After cells are formed in the basal layer, they begin to migrate toward the skin surface, until they are eventually sloughed off. As they undergo this migration, they become progressively more dehydrated and keratinized. When they reach the surface, just prior to being discarded, they form a thin layer of dense, metabolically inactive cells approximately ten microns (10-15 cells) thick. This layer is called the stratum corneum or the "cornified layer". As a result of the high degree of keratinization of the cells which comprise the stratum corneum, a formidable barrier is created. Therefore, penetration via the nonpolar route, i.e., across the membrane of these cells, remains most difficult.

The problem is even more difficult when trying to deliver pharmaceutical agents through the unguis, the horny cutaneous plates on the dorsal surface of the distal end of the terminal phalanx of a finger or toe (fingernails and toenails). They are made up of flattened epithelial scales developed from specialized epithelial cells called the matrix. The thick and hardened nature of nails renders access through, and to the area below, nearly impossible with current topical formulations. The subject of the present disclosure has the advantage of being able to delivery pharmaceutical agents through the unguis to heretofore minimally accessible disease targets.

Accordingly, in an effort to take advantage of this route of administration and overcome the obstacles the skin and nails naturally provide, the art has turned to the use of specifically selected vehicles and carriers into which the pharmaceutical active is incorporated so that the vehicle or carrier aids in, or at a minimum does not adversely affect, the penetration of the selected active agent. The art recognizes that to a vast degree the rate of percutaneous delivery of a pharmaceutical active can be significantly decreased by the selection of an improper vehicle.

Because of the ease of access, dynamics of application, large surface area, vast exposure to the circulatory and lymphatic networks, and non-invasive nature of the treatment, the delivery of pharmaceutically-active agents through the skin has long been a promising concept. This is true whether the bioavailability desired is systemic or dermal, regional or local.

The advantages of this form of delivery include, but are not limited to: avoidance of the risks associated with parenteral treatment; elimination of the inconveniences of parenteral treatment; avoidance of the variable rates of absorption and metabolism inherent in oral treatment; increasing the continuity of drug administration by permitting delivery of agents with short biological half-lives; and elimination of gastrointestinal irritation resulting from exposing the gastrointestinal tract to pharmaceutical actives, preservatives, tableting agents, and the like. Most importantly, topical delivery possesses the potential for effectively treating conditions which are local in nature (or which exhibit local manifestations), systemically as well as locally with the same treatment regimen. Thus, effective compositions to deliver pharmaceutical agents are highly sought after.

Although various compositions have been suggested for the precutaneous delivery of certain pharmaceutically active agents, a need exists for achieving enhanced delivery of cosmetic and pharmaceutical agents to the skin for local treatment of skin conditions and diseases. In particular, the composition should be easy to apply topically in a quantitative amount, to allow the active agent to rapidly permeate the skin to get where the agent is needed, to have a pleasant odor and appearance, and to not require cleansing to remove the agent.

This combination of these desired characteristics is difficult to achieve.

SUMMARY

The present disclosure relates to a composition for the local delivery of at least one cosmetic or pharmaceutical agent or both. The composition comprises at least two biocompatible organic solvents, a polar lipid, at least one surfactant, water, urea and a thickener. The organic solvents comprise an ester and a dihydric and/or polyhydric alcohol. The composition comprises about 2 to about 30% by weight of the ester and about 0.5 to about 20% by weight of the dihydric and/or polyhydric alcohol.

The present disclosure also relates to a method of delivering an active agent into and through the epidermis or ungual tissue of a human or animal comprising topically applying to the skin or to the nail of the human or animal a composition comprising a cosmetic and/or pharmaceutically active agent and the composition disclosed above.

Another aspect of the present disclosure relates to a composition comprising the above disclosed delivery composition and a cosmetic and/or pharmaceutically active agent. The pH of the composition containing the active agent is typically about 5.5 to about 7.5.

A still further aspect of the present invention relates to a method for making a composition suitable for the cutaneous delivery of a cosmetic and/or pharmaceutically active agent which comprises:

a. Dissolving a polar lipid at least in two biocompatible organic solvents comprising at least one ester and at lease one dihydric or polyhydric alcohol;
b. Adding one or more surfactants to the composition of step (a);
c. Dissolving a cosmetic pharmaceutical and/or active compound in the solvent-polar lipid, surfactant mixture of step (b);
d. Adding a urea and at least one thickener to water;
e. Combining the compositions from c and d and adjusting the pH to about 5.5 to about 7.5, if necessary.

The present disclosure further relates to a composition prepared by the above disclosed method.

Other objections and advantages of the present disclosure will become readily apparent to those skilled in this art from the following detailed description, wherein it is shown and described only the preferred embodiments, simply by way of illustration of the best mode contemplated of carrying out the disclosure. As will be realized, the disclosure is capable of other and different embodiments, and its several details are capable of modifications in various obvious respects, without departing from the disclosure. Accordingly, the description is to be regarded as illustrative in nature and not as restrictive.

BEST AND VARIOUS MODES

By "topical administration", as used herein, is meant directly laying or spreading upon epidermal or ungual tissue, especially outer skin, nails, or membrane, including the skin or membrane of the oral, rectal, or vaginal cavities.

By "safe and effective amount", as used herein, is meant a sufficient amount of the composition to provide the desired local therapeutic activity and performance at a reasonable benefit/risk ratio attendant any medical treatment. Within the scope of sound medical judgment, the amount of active agent used will vary with the particular condition being treated, the severity of the condition, the duration of the treatment, the specific active ingredient(s) employed, its or their concentration, the condition of the patient, concurrent therapies being administered, and like factors within the specific knowledge and expertise of the patient or the attending physician.

By "toxicologically- or pharmacologically-acceptable", as used herein, is meant the pharmaceutical actives, as well as other compatible drugs, medicaments or inert ingredients which the term describes are suitable for use in contact with the tissues of human and lower animals without undue toxicity, irritation, allergic response, and the like, commensurate with a reasonable benefit/risk ratio.

By the term "comprising", as used herein, is meant that various other compatible cosmetics, drugs and medicaments, as well as inert ingredients, occlusive agents, and cosmetic vehicles, can be conjointly employed in the compositions and methods of this invention, as long as the critical binary penetration enhancement vehicle and cosmetic or pharmaceutical active are used. The term "comprising" thus encompasses and includes the more restrictive terms "consisting of" and "consisting essentially of" which characterize the use of the essential ingredients in the manner disclosed herein.

By "afflicted sites", as used herein, is meant a localized area of pathology, discomfort, infection, inflammation or lesion, and the immediately surrounding area.

By "application sites", as used herein, is meant a site suitable for application via a mechanical sustained release device or dressing, e.g., behind the ear, on the arm, back, top of the foot, etc.

By "penetration-enhancing", as used herein, is meant that the binary penetration enhancing carriers of this disclosure provide marked transepidermal, transungual or percutaneous delivery of an incorporated active, when compared to other compositions at equal chemical potential. This latter aspect is important, since varying solubilities of cosmetics or drugs in different vehicles will necessarily affect their transport across skin or through nails. Thus, for example, if a drug is soluble in vehicle A to the extent of 24%, and in vehicle B to the extent of 4%, were the compositions to be compared at equal percentage concentration, rather than equal chemical potential, the lower solubility carrier will show a misleading six-fold difference in transport over the more soluble vehicle. The simplest way of assuring equal chemical potential for evaluating penetration enhancement is to use saturated solutions or solutions of equal percentage of saturation of pharmacological active in the various vehicles.

By "substantially free", as used herein, is meant that the penetration-enhancing compositions of the present invention contains less than about 10%, preferably less than 3.5%, more preferably less than about 1%, and most preferably less than about 0.5%, of any specific compound, or member of the group of compounds, described by this term.

As used herein, all percentages and ratios are by weight of the total composition unless otherwise specified.

The terms "active", "pharmaceutical active", "pharmacological active", "pharmaceutical agent", "pharmacological agent", "pharmaceutically-, or pharmacologically-active agent", "chemical agent", and "therapeutic agent", are used interchangably herein.

The compositions of this disclosure contain a cosmetic agent and/or pharmaceutically-active agent capable of producing or possessing local activity, in a binary vehicle or carrier. The vehicle on carrier comprises a polar lipid, such as lecithin or phosphotidylcholine, and two biocompatible organic solvents, one chosen from the group of esters and one chosen from the group of liquid dihydric and polyhydric alcohols, a preservative, water, a thickener and urea, at a pH of between about 5.5 and 7.5 and preferably between 6.0 and 7.0. The compositions of this disclosure may additionally contain other optional components that reduce skin irritation, or enhance their cosmetic appeal or acceptability, e.g, pigments, fragrances, perfumes, and the like.

Typical polar lipids employed are lecithin and phosphotidylcholine. Preferably, the lecithin or phosphatidylcholine is of a high quality, pharmaceutical grade. Appropriate lecithin and phosphatidylcholine maybe obtained as commercially available soya lecithin or soya phosphatidylcholine. Preferably, soya lecithin is used in the composition of this invention.

The biocompatible organic ester solvents may be any non-toxic ester in which the polar lipid, the cosmetic or pharmaceutically active compound and urea are soluble, and which assists as a solubilizing vehicle for carrying cosmetic or pharmaceutically active compounds across the skin of a mammal.

Typically the esters are fatty mono esters having a structure, obtainable by replacing the active hydrogen of a fatty acid having 4 to 22 carbon atoms and more typically having 8 to 18 carbon atoms by the alkyl group of a monohydric alcohol, particular example being 12 carbon atoms. The fatty acid can be saturated or unsaturated and more typically is saturated. The monohydric alcohol typically contains 2 to 8 carbon atoms and more typically 2 to 5 carbon atoms, a particular example being 3 carbon atoms.

Acceptable esters for this purpose include, but are not limited to isopropyl esters. Preferably, the ester is isopropyl myristate or isopropyl palmitate, with isopropyl myristate being particularly preferred.

The biocompatible organic dihydric and polyhydric alcohol solvents may be any non-toxic di or polyalcohol in which the polar lipid and the active compound are soluble, and which assists as a solubilizing vehicle for carrying active compounds across the skin of a mammal. Acceptable dihydric and polyalcohols for this purpose include, but are not limited to di- and tri-alcohol alkanes. Typically the alcohols contain 3 to 8 carbon atoms and more typically 3 to 5 carbon atoms and are saturated alcohols. Preferably, the polyalcohol is propylene glycol or glycerol, with propylene glycol being particularly preferred.

The compositions of the present disclosure typically contain about 2 to 30% by weight and more typically 4 to 10% by weight of the ester and about 0.5 to about 20% by weight, more typically 1 to about 20% weight, and even more typically 1 to about 10% weight of the alcohol. Many of the compositions contain about 2 to about 20% by weight or, 2 to about 10% weight of the alcohol. Compositions according to the present disclosure exhibit reduced skin irritation.

In preparing the composition of this disclosure, the polar lipid is typically dissolved in the organic ester solvent and di or polyalcohol solvent at mass ratios from about 5:1:1 to about 1:5:5. Preferably, the polar lipid and organic ester solvent and polyalcohol solvent are mixed in equal mass ratios. Thus, in one embodiment of the invention, soya lecithin, isopropyl myristate, and propylene glycol are mixed in equal mass ratios and mixed until the lecithin is evenly distributed. This is referred to as the solvent-polar lipid mixture.

Depending on the nature of the cosmetic or pharmaceutically active compound and the desired characteristics of the final formulation, a surfactant can be included in the formulation at a concentration of between about 1-20% of the final composition mass. In the formulation including a polycationic active agent, it has been found, according to this disclosure that non-ionic or cationic surfactants are preferred. In the case of other active ingredients, on the other hand, anionic, cationic or non-ionic surfactants are quite acceptable. Preferably, the surfactant is one which is compatible with administration in vivo without elicitation of undesirable side effects. One preferred surfactant is docusate sodium and its more water soluble form, docusate sodium benzoate. Other appropriate ionic or non-ionic surfactants, such as polysorbate 80, Tween 80, docusate calcium, tetradecyltrimethylammonium bromide, pentaoxyetylene glycol monododecyl ether, or triethanolamine laureth sulfate. Once the surfactant is thoroughly dispersed in the solvent-polar lipid mixture, the cosmetic or pharmaceutically active compound may be added and dissolved.

The dosage of the cosmetic or pharmaceutical agent will, of course, vary depending upon known factors, such as the cosmetic or pharmaceutical agent characteristics of the particular agent; the age, health and weight of the recipient; the nature and extent of the symptoms; the kind of concurrent treatment; the frequency of treatment; and the effect desired. A daily dosage of active ingredient can be expected to be about 0.001 to 1000 milligrams (mg) per kilogram (kg) of body weight, with the more typical dose being 0.1 to about 30 mg/kg.

The active agent is typically present in amounts of about 0.001 to about 30%, more typically about 0.001 to about 20%, and even more typically about 0.5 to 12% by weight based upon the total of the delivery system and active agent. For solid active ingredients, this is most easily achieved by heating an aliquot of the surfactant-solvent-polar lipid mixture and adding, on a mass basis, an amount of active compound equal to about 0.01 to 30% of the mass of the surfactant-solvent-polar lipid and mixing until completely dissolved. Thus, for example, about 1-20 grams of nifedipine in a powdered form is added to about 100 grams of heated 1:0.5:0.5 soya lecithin:isopropyl myristate:propylene glycol and allowed to dissolve with stirring.

Some exemplary active agents include vasodilating agents such as glyceryl trinitrate and nifedipine; antimicrobial or antifungal agents such as ciclopirox, itraconazole, metronidazole, miconazole and allylamines such as, naftifine and terbinafine and salts thereof; inhibitors of cell growth or proliferation, such as 2-deoxy-D-glucose; inhibitors of polyamine transport; inhibitors of polyamine synthesis; antizyme inducers; decalcifying skin agents such as lactic acid; anti-inflammatory agents such as ibuprofen and ketoprofen; topical anaesthetics such as lidocaine; steroidal anti-inflammatory compounds, such as cortisone; peptides, proteins, or hormones, such as platelet factor 4; substance P antagonists such as capsaicin; muscle relaxants such as cyclobenzaprine; anti-inflammatory analgesics such as diclofenac sodium and phosphodiesterase inhibitors such as sudenifil.

In the event a volatile active agent or proteinaceous active agent is used, adding the active agent to a relatively warm solution of surfactant-solvent polar lipid mixture is not usually desired as this might decrease the amount of active agent in the final formulation.

By way of specific examples, in the case of the active nitroglycerin, the active is available in the form of a 10% concentration in propylene glycol, which can be added directly to the polar lipid-solvent-surfactant mixture.

The amount of a vasodilator for the treatment of peripheral arterial diseases, including Raynaud's Disease, diabetic paresthesia, and night leg cramps is typically about 0.2 to about 1.8% of the composition.

The amount of antimicrobial agent or antifungal agent for the treatment of infectious diseases of the skin and nails, including onychomycosis, athlete's foot, rosacea, and vaginomycosis is typically about 0.5 to about 12% by weight.

The amount of an inhibitor of cell growth or proliferation for treatment of actinic keratosis is about 0.001 to about 10% of weight.

The amount of an inhibitor of polyamine transport is typically about 0.001 to about 5% by weight. The amount of an inhibitor of polyamine synthesis for the treatment of an auto-mimmune disease, including cutaneous lupus erythrematosus, urticaria, psoriasis, and atopic dermatosis is typically about 0.001 to about 5% by weight.

The amount of a decalcifying skin agent, such as lactic acid, for the treatment of dry skin conditions, including xerosis, scleroderma, and ichthyosis is typically about 0.5 to about 10% by weight.

It is further understood that two or more different types of active agents can be employed in order to treat more than one condition at the same time. For instance, two or more active agents can be used to treat inflammatory, autoimmune, infectious and/or dry skin conditions simultaneously.

After addition of the cosmetic or pharmaceutically active compound, an amount of urea, preferably as a thickened aqueous solution, can be added to the surfactant-solvent-polar lipid mixture. The urea is typically added so that the urea concentration about 1% to about 15% and more typically about 5% and 10% by mass of the final composition mass.

The thickener is selected from common National Formulary thickening agents including, but not limited to appropriate polymer weights of polyethylene glycol, polyvinylpyrrolidone, carbomer and methylcellulose. The amount of thickener is typically about 0.05 to about 5% by weight.

Thus in a specific example, about 5 grams of a 10% aqueous solution of urea, containing 0.7% Carbomer 934, is added to about 100 grams of the surfactant-solvent-polar lipid mixture with dissolved pharmaceutically active compound. In some instances, the pharmaceutically active agent will more readily dissolve if added after addition of the aqueous urea solution, and in other instances before the addition of aqueous urea solution. In any event, this is a choice readily made by those skilled in the art, once aware of the present disclosure, depending on the particular formulation being prepared and the solubility characteristics of the particular cosmetic or pharmaceutically active compound being solubilized. If the active agent is a protein, it will be necessary to test the retention of biological activity of the protein upon exposure to the particular urea concentration used in this formulation as the chaotropic properties of urea are known to denature some proteins. Such a determination is easily conducted by one of ordinary skill in the art.

Upon formulation of the above described composition with the cosmetic or pharmaceutically active agent, the pH is adjusted to typical pH of about 5.5 to about 7.5 and more typically to a 6.0 to 7.0. This can be accomplished, for example, by addition of a base such as aqueous sodium hydroxide and trolamine, as the compositions initially tend to have an acid pH. However, if the pharmaceutically active agent tends to produce very alkaline solutions, addition of an acid to reduce the pH would be desirable. This can be accomplished by addition of an acid such as citric acid or a biological buffer such as sodium carbonate or potassium phosphate. With the composition in a pH range of about 5.5 to 7.5, the formulation thickens and forms a smooth, viscous gel for topical administration.

In one embodiment of the disclosure, the composition is formulated with a vasodilating agent, such as glyceryl trinitrate. Such formulation is rapidly absorbed through the skin and provides local vasodilation, increases in blood flow, and restoration of normal temperature to an extremity with low blood flow. In another embodiment of the invention, the composition is formulated with an anti-infective agent. Such formulation is rapidly absorbed through the skin, or somewhat more slowly through the nails to provide local delivery to kill invading microorganisms such as fungi or bacteria.

By routine experimentation, using the recited elements of this composition, those skilled in the art, once aware of the present disclosure, will be able to make specific gels of essentially any active ingredient or combination thereof for a wide variety of typical applications. In addition, it is understood that the compositions can contain auxiliary agents including those conventionally known and/or used in this art such as, but not limited to, preservatives and fragrances.

For ease of preparation, it is convenient to prepare a first gel composition, referred to herein as "MQX-GEL", which can be used to add to other components in the formulation of a final composition for topical administration. There are several possible formulations of the MQX-GEL. For example, a MQX-GEL may be prepared by mixing lecithin organogel (L.O.), as a 1:1:1 (m/m/m) mixture of lecithin, isopropyl myristate and propylene glycol, with LID oil (a 1:1 [m/m] mixture of L.O. and docusate sodium), dissolving additional surfactant and/or docusate sodium powder into this mixture, and then adding thickened aqueous urea.

In one embodiment of the MQX-GEL formulation, the final concentrations are: L.O.=30%; docusate sodium=9%; urea=5%; thickener=1%; and water=55%. These ratios may easily be varied such that the final amounts of each component are as follows: L.O.=15-50%; docusate sodium and/or another surfactant=3-15%; urea=1-15%; thickener=0.5-5%; and water=40-65%. The solubilized active ingredients may then be added to MQX-GEL. Excipients which may be useful in solubilizing the active ingredient include L.O., propylene glycol, isopropyl myristate, peppermint oil, glycerin, and/or polyethylene glycol. A homogeneous mixture is then made by carefully blending the various components.

Once the formulations described above have been prepared, use of the formulations is a simple matter of applying the formulation to affected areas where cutaneous delivery of the pharmaceutically active agent is desired. Thus, in the case of Raynaud's phenomenon, formulations containing glyceryl trinitrate are rubbed over the affected area such as the fingers of the hands. Treatment is repeated as symptoms reappear or when used as a prophylactic treatment, just before symptoms may appear. In use of formulations prepared according to this invention, normal blood flow in the fingers of the Raynaud's patient has been restored within five minutes of application.

In another aspect of this invention, an anti-fungal anti-microbial compound is formulated for delivery to toe nails infected with fungus. In nine-month treatments, doctors and patients across the country have confirmed almost complete reduction in fungal infection. This is in contrast to results observed with current commercial topical formulations with this same active ingredient that provide very modest reduction in fungal infection in the same time frame.

A still further indication for the organogel compositions of this disclosure is for treating nail psoriasis. For such indication, active ingredients to use include one or more of the compounds useful in the treatment of psoriasis, typically in amounts of about 0.0005% to 10% depending upon the type of agent, such as, corticosteroids (Clobetasol propionate about 0.005-about 0.05%, Betamethasone dipropionate about 0.005-about 0.05%, Diflorasone diacetate about 0.005-about 0.05%, Halcinonide about 0.01-about 0.1%, Desoximetasone about 0.005-about 0.5%, Triamcinolone acetonide about 0.01-about 0.5%), anti-proliferative cancer agents (flourouracil, methotrexate, polyamine synthesis and transport inhibitors, antizyme inducers, each about 0.05-about 5.0%), retinoids (tazarotene, acetretin), vitamin D analogs (calcipotriene); combinations of these agents and also a combination with an antifungal agent (e.g. miconazole, ciclopirox, terbinafine, each at about 0.5-about 10%).

In another aspect of this invention, a composition comprising an antibacterial agent is prepared, for example, by inclusion of bacitracin or another appropriate antibiotic. This allows for penetration of the antibacterial agent to sites of infection induced by puncture wounds.

In general, compositions of this invention are provided at a concentration of between about 0.001% to 30% by weight of active compound. In addition, compositions comprising more than one active ingredient are within the scope of this disclosure and could be administered to a recipient in need of more than a single active treatment at one localized spot. Thus, for example, a composition comprising a vasodilating agent and an antifungal would both provide relief from fungal infection and will facilitate long-term relief by restoring blood flow and the flow of nutrients to the affected area.

It is contemplated that the compositions of this disclosure are applied topically as frequently as required as long as local reactions or toxicity due to the active ingredient do not become a problem. Thus, for example, a more rigorously monitored regimen of application may be required when an anti-neoplastic compound is being administered than when a readily metabolized non-toxic compound such as ketoprofen is administered. In the latter case, it would be acceptable for a person in need of such treatment to topically apply the composition as frequently as needed to achieve relief from local pain or inflammation.

While the foregoing description generally describes how to make and use the compositions and formulations of this disclosure, the following examples are provided to more specifically point out how to practice the invention. However, it should be clearly understood that the scope of this disclosure, as defined by the claims appended hereto, is not to be limited to the specifics of the following examples. Further, it should be understood that, in the specific compositions described and claimed, the percentages of active and other ingredients could be within at least a 10% different amount while still achieving an objective equivalent to the specifically disclosed compositions.

The following non-limiting examples are presented to further illustrate the present disclosure:

EXAMPLE 1

Preparation of MQX-GEL

|  | 500 gm |
| --- | --- |
| LID Oil* | 50 gm |
| Lecithin organogel** (L.O.) | 100 gm |
| Docusate sodium powder | 50 gm |
| Urea | 50 gm |
| Thickener | 5 gm |
| Distilled water | 245 ml |

*LID oil is a 1:1 mixture of lecithin organogel:docusate sodium on a mass basis.
**L.O. is a 1:1:1 mixture of lecithin, isopropyl myristate and propylene glycol.

1. The LID was added to L.O. and heated.

2. Docusate sodium powder was added, and the mixture was stirred until smooth.

3. Thickener and urea were completely dissolved in water, heated, and added to step 2 with stirring.

4. pH was adjusted to between 6.5 to 6.9.

MQX-GEL may just as easily be prepared as follows:

|  | 1000 gm |
| --- | --- |
| L.O. | 250 gm |
| Docusate sodium benzoate powder | 150 gm |
| Urea | 100 gm |
| Thickener | 10 gm |
| Distilled water | 490 ml |

The L.O. was heated and the docusate sodium benzoate powder was stirred into the heated L.O. until a smooth solution is prepared. The water was heated and the thickener and urea were dissolved into the water, and the thickened urea solution was then thoroughly mixed with the docusate sodium containing solution of L.O. The result was a consistent, transparent, amber colored gel with a pH of about 6.0.

A further method of making MQX-GEL is as follows:

|  | 1000 gm |
| --- | --- |
| L.O. | 100 gm |
| LID | 300 gm |
| Urea | 100 gm |
| Thickener | 10 gm |
| Distilled water | 490 gm |

The LID and L.O. were mixed well and a heated solution of water, the thickener and the urea was prepared and added to the LID-L.O. solution. The result was a consistent, transparent, amber colored gel with a pH of about 6.0.

EXAMPLE 2

Preparation of 1.2% Glyceryl Trinitrate Gel

|  | 500 gm |
| --- | --- |
| Glyceryl Trinitrate (as 10% active in propylene glycol or 54.0 gm of propylene glycol) | 6.0 gm |
| Lecithin organogel (L.O.) | 90.0 gm |
| Docusate Sodium | 22.6 gm |
| Urea | 25.1 gm |
| Carbomer 934 | 3.5 gm |
| Methylcellulose | 4.4 gm |
| Water, distilled | 294.4 gm |

1. Docusate sodium is added to L.O. and stirred to obtain a clear solution.

2. Glyceryl trinitrate (as 10% active in propylene glycol) is added to solution of step 1.

3. Urea is added to distilled water, with heating and stirring to obtain a uniform solution.

4. Carbomer 934 and Methylcellulose are added to thicken the urea-water of step 3.

5. The lecithin organogel with the active component from step 2 is combined with the thickened aqueous urea from step 4 to form a uniform mixture.

6. The pH is adjusted to 6.5 with dilute aqueous NaOH to form an elegant thick gel.

EXAMPLE 3

Preparation of 0.5% Glyceryl Trinitrate Gel

|  | 500 gm |
| --- | --- |
| Glyceryl Trinitrate (as 10% active in propylene glycol or 22.5 gm of propylene glycol) | 2.5 gm |
| Lecithin organogel (L.O.) | 125.0 gm |
| Docusate Sodium | 22.6 gm |
| Urea | 25.1 gm |
| Carbomer 934 | 3.5 gm |
| Methylcellulose | 4.4 gm |
| Water, distilled | 294.4 gm |

The same method of combining the ingredients is used as described in example 2.

MQX-GEL can also be prepared with other ratios of the three constituents of the lecithin organogel. In the following example, the ratio of lecithin organogel (L.O. #2), is a 1:0.9:0.1 (m/m/m) mixture of lecithin, isopropyl myristate and propylene glycol, with LID oil (a 1:1 [m/m] mixture of L.O.#2 and docusate sodium), dissolving additional surfactant and/or docusate sodium powder into this mixture, and then adding thickened aqueous urea.

In this embodiment of the MQX-GEL formulation, the final concentrations are: L.O.#2=25%; docusate sodium=10%; urea=10%; thickener=1%; and water=54%. These ratios also may easily be varied such that the final amounts of each component are as follows: L.O.#2=15-50%; docusate sodium and/or another surfactant=3-15%; urea=1-15%; thickener=0.5-5%; and water=40-65%. The solubilized active ingredients may then be added to MQX-GEL. Excipients which may be useful in solubilizing the active ingredient include L.O.#2, propylene glycol, isopropyl myristate, peppermint oil, glycerin, and/or polyethylene glycol. A homogenous mixture is then made by carefully blending the various components.

EXAMPLE 4

Preparation of Another 1.2% Glyceryl Trinitrate Gel

|  | 500 gm |
| --- | --- |
| Glyceryl Trinitrate (as 10% active in propylene glycol or 54.0 gm of propylene glycol) | 6.0 gm |
| L.O. #2 | 115.0 gm |
| Docusate Sodium | 45.0 gm |
| Urea | 45.0 gm |
| Carbomer 934 | 3.5 gm |
| Methylcellulose | 4.4 gm |
| Water, distilled | 227.1 gm |

The same method of combining the ingredients is used as in example 2.

EXAMPLE 5

Preparation of 0.5% Glyceryl Trinitrate Gel

|  | 500 gm |
| --- | --- |
| Glyceryl Trinitrate (as 10% active in propylene glycol or 22.5 gm of propylene glycol) | 2.5 gm |
| L.O. #2 | 150.0 gm |
| Docusate Sodium | 45.0 gm |
| Urea | 45.0 gm |
| Carbomer 934 | 3.5 gm |
| Methylcellulose | 4.4 gm |
| Water, distilled | 227.1 gm |

The same preparation method was used in this example as in the previous one.

EXAMPLE 6

Preparation of 8.0% Ciclopirox Gel

|  | 500 gm |
| --- | --- |
| Ciclopirox | 40.0 gm |
| L.O. #2 | 128.9 gm |
| Docusate Sodium | 45.0 gm |
| Urea | 45.0 gm |
| Carbomer 934 | 2.6 gm |
| Methylcellulose | 1.5 gm |
| Water, distilled | 237.0 gm |

1. Docusate sodium is added to L.O.#2 and stirred to obtain a clear solution.

2. Ciclopirox is added to solution of step 1.

3. Urea is added to distilled water, with heating and stirring to obtain a uniform solution.

4. Carbomer 934 and Methylcellulose are added to thicken the urea-water of step 3.

5. The lecithin organogel with the active from step 2 is combined with the thickened aqueous urea from step 4 to form a uniform mixture.

6. The pH is adjusted to 6.5 with dilute aqueous NaOH to form an elegant thick gel.

EXAMPLE 7

Preparation of 15.0% Lactic Acid Gel

|  | 500 gm |
| --- | --- |
| Lactic Acid | 75.0 gm |
| L.O. #2 | 118.9 gm |
| Docusate Sodium | 30.0 gm |
| Urea | 45.0 gm |
| Carbomer 934 | 2.6 gm |
| Methylcellulose | 1.5 gm |
| Water, distilled | 232.0 gm |

The same method of preparation is used as in example 6.

EXAMPLE 8

Preparation of 8% Ciclopirox, 1% Glyceryl Trinitrate Gel

|  | 500 gm |
| --- | --- |
| Glyceryl Trinitrate (as 10% active in propylene glycol or 45.0 gm of propylene glycol) | 5.0 gm |
| Ciclopirox | 40.0 gm |
| L.O. #2 | 115.0 gm |

-continued

|  | 500 gm |
|---|---|
| Docusate Sodium | 35.0 gm |
| Urea | 35.0 gm |
| Carbomer 934 | 2.8 gm |
| Methylcellulose | 1.7 gm |
| Water, distilled | 220.5 gm |

1. Docusate sodium is added to L.O.#2 and stirred to obtain a clear solution.

2. Ciclopirox and Glyceryl trinitrate, as 10% solution in propylene glycol, is added to solution of step 1.

3. Urea is added to distilled water, with heating and stirring to obtain a uniform solution.

4. Carbomer 934 and Methylcellulose are added to thicken the urea-water of step 3.

5. The lecithin organogel with the actives from step 2 is combined with the thickened aqueous urea from step 4 to form a uniform mixture.

6. The pH is adjusted to 6.5 with dilute aqueous NaOH to form an elegant thick gel.

EXAMPLE 9

Preparation of 10% Ibuprofen, 0.5% Glyceryl Trinitrate Gel

|  | 500 gm |
|---|---|
| Glyceryl Trinitrate (as 10% active in propylene glycol or 22.5 gm of propyleneglycol) | 2.5 gm |
| Ibuprofen | 50.0 gm |
| L.O. #2 | 135.0 gm |
| Docusate Sodium | 15.0 gm |
| Urea | 35.0 gm |
| Carbomer 934 | 2.8 gm |
| Methylcellulose | 1.7 gm |
| Water, distilled | 220.5 gm |

1. Docusate sodium and ibuprofen are added to L.O.#2 and stirred to obtain a clear solution.

2. Glyceryl trinitrate, as 10% solution in propylene glycol, is added to solution of step 1.

3. Urea is added to distilled water, with heating and stirring to obtain a uniform solution.

4. Carbomer 934 and Methylcellulose are added to thicken the urea-water of step 3.

5. The lecithin organogel with the actives from step 2 is combined with the thickened aqueous urea from step 4 to form a uniform mixture.

6. The pH is adjusted to 6.5 with dilute aqueous NaOH to form an elegant thick gel.

EXAMPLE 10

Preparation of 5.0% 2-Deoxy-D-Glucose Gel

|  | 500 gm |
|---|---|
| 2-Deoxy-D-Glucose | 25.0 gm |
| L.O. #2 | 128.9 gm |
| Docusate Sodium | 45.0 gm |
| Urea | 45.0 gm |
| Carbomer 934 | 2.6 gm |
| Methylcellulose | 1.5 gm |
| Water, distilled | 252.0 gm |

1. Docusate sodium is added to L.O.#2 and stirred to obtain a clear solution.

2. 2-Deoxy-D-Glucose is added to solution of step 1.

3. Urea is added to distilled water, with heating and stirring to obtain a uniform solution.

4. Carbomer 934 and Methylcellulose are added to thicken the urea-water of step 3.

5. The lecithin organogel with the active from step 2 is combined with the thickened aqueous urea from step 4 to form a uniform mixture.

6. The pH is adjusted to 6.5 with dilute aqueous NaOH to form an elegant thick gel.

Additional formulations for treating onychomycosis that can be prepared along the lines of Example 6 are presented below.

EXAMPLE 11

Formulation of 2% Miconazole Gel

A formulation is prepared along the lines of Example 6 containing 2% miconazole nitrate, 48.5% distilled water, 10% urea, 0.45% carbopol, 8.8% isopropyl myristate, 9.8% lecithin, 19.1% docusate sodium, 0.4% polysorbate 80, 1.0% propylene glycol, 0.8% trolamine and 0.12% 1.0 N NaOH.

EXAMPLE 12

Formulation of 2% Naftifine Gel

A formulation is prepared along the lines of Example 6 containing 2% naftifine hydrochloride, 48.5% distilled water, 10% urea, 0.45% carbopol, 8.8% isopropyl myristate, 9.8% lecithin, 19.1% docusate sodium, 0.4% polysorbate 80, 1.0% propylene glycol, 0.8% trolamine and 0.12% 1.0 N NaOH.

EXAMPLE 13

Formulation of 5% Terbinafine Gel

A formulation is prepared along the lines of Example 6 containing 5% terbinafine hydrochloride, 45.5% distilled water, 9.75% urea, 0.7% carbopol, 8.8% isopropyl myristate, 9.8% lecithin, 19.1% docusate sodium, 0.4% polysorbate 80, 1.0% propylene glycol, 0.8% trolamine and 0.12% 1.0 N NaOH.

EXAMPLE 14

Formulation of 2% Ciclopirox Gel

A formulation is prepared along the lines of Example 6 containing 2% ciclopirox olamine, 48.5% distilled water, 10% urea, 0.45% carbopol, 8.8% isopropyl myristate, 9.8% lecithin, 19.1% docusate sodium, 0.4% polysorbate 80, 1.0% propylene glycol, 0.8% trolamine and 0.12% 1.0 N NaOH.

EXAMPLE 15

Formulation of 4% Ciclopirox Gel

A formulation is prepared along the lines of Example 6 containing 4% ciclopirox olamine, 46.5% distilled water, 10% urea, 0.45% carbopol, 8.8% isopropyl myristate, 9.8% lecithin, 19.1% docusate sodium, 0.4% polysorbate 80, 1.0% propylene glycol, 0.8% trolamine and 0.12% 1.0 N NaOH.

EXAMPLE 16

Formulation of 0.001% Betamethasone Dipropionate and 2.5% Methotrexate for Treating Nail Psoriasis A formulation along the lines of example 11 can be prepared by replacing the 2% miconazole with 0.001% betamethasone dipropionate and 2.5% methotrexate.

EXAMPLE 17

Formulation of 0.001% Betamethasone Dipropionate, 2.5% Methotrexate, and 2% Miconazole for Treating Nail Psoriasis A formulation along the lines of example 11 can be prepared by replacing the 2% miconazole with 0.001% betamethasone dipropionate, 2.5% methotrexate, and 2% miconazole.

The foregoing description illustrates and describes the present disclosure. Additionally, the disclosure shows and describes only the preferred embodiments of the disclosure, but, as mentioned above, it is to be understood that it is capable of changes or modifications within the scope of the concept as expressed herein, commensurate with the above teachings and/or the skill or knowledge of the relevant art. The embodiments described hereinabove are further intended to explain best modes known of practicing the invention and to enable others skilled in the art to utilize the disclosure in such, or other, embodiments and with the various modifications required by the particular applications or uses disclosed herein. Accordingly, the description is not intended to limit the invention to the form disclosed herein. Also, it is intended that the appended claims be construed to include alternative embodiments.

All publications, patents and patent applications cited in this specification are herein incorporated by reference, and for any and all purposes, as if each individual publication, patent or patent application were specifically and individually indicates to be incorporated by reference. In the case of inconsistencies, the present disclosure will prevail.

What is claimed as new and desired to be protected by Letters Patent of the United States is:

1. A composition suitable for the delivery of at least one cosmetic agent or pharmaceutical agent or both through the skin or nails of a mammal, which comprises two biocompatible organic solvents, 6 to 30% by weight of lecithin, 0.5 to 19% by weight of at least one or more surfactant, wherein said surfactant comprises a docusate, 40 to 65% by weight of water, 1 to 15% by weight of urea and 0.05 to 5% by weight of thickener; wherein the organic solvents comprise 2 to 30% of isopropyl myristate and 0.5 to 20% of propylene glycol.

2. The composition of claim 1, wherein at least one surfactant is selected from the group consisting of docusate sodium, docusate sodium benzoate, and docusate calcium.

3. The composition according to claim 1, wherein the thickener is selected from the group of polyethylene glycol, methyl cellulose, and carbomer.

4. The composition of claim 1, further comprising at least one of a cosmetic agent or pharmaceutical agent or both.

5. The composition of claim 1, wherein the amount of the cosmetic agent or pharmaceutical agent or both is about 0.001 to about 30% by weight.

6. The composition of claim 1, having a pH of about 5.5 to about 7.5.

7. The composition of claim 1, wherein the pH is about 6 to about 7.

8. The composition of claim 1, further comprising at least 0.2-1.8% by weight of a vasodilating agent.

9. The composition of claim 8, wherein the vasodilating agent is glyceryl trinitrate.

10. The composition of claim 1, further comprising 1 to 12% by weight of an antimicrobial agent.

11. The composition of claim 10, wherein the antimicrobial agent is selected from the group consisting of ciclopirox, miconazole, itraconazole, metronidazole, an allylamine and mixtures thereof and pharmaceutically acceptable salts thereof.

12. The composition of claim 10, wherein the antimicrobial agent is selected from the group consisting of ciclopirox, miconazole, terbinafine and naftifine and mixtures thereof and salts thereof.

13. The composition of claim 1, further comprising 0.001-10.0% by weight of an inhibitor of cell growth or proliferation.

14. The composition of claim 13, wherein said inhibitor is 2-deoxy-D-glucose.

15. The composition of claim 1, further comprising 0.001-5.0% by weight of an inhibitor of polyamine transport or 0.005-5.0% by weight of an inhibitor of polyamine synthesis.

16. The composition of claim 1, further comprising 0.001-5.0% by weight of an antizyme inducer.

17. The composition of claim 1, further comprising 0.5-10% by weight of a decalcifying skin agent.

18. The composition of claim 17, wherein the decalcifying skin agent is lactic acid.

19. The composition of claim 1, further comprising an effective amount of one or more psoriasis treating agent(s).

20. The composition, according to claim 19, wherein the psoriasis treating agent comprises betamethasone dipropionate or methotrexate or both.

21. The composition, according to claim 19 which further comprises metronidazole.

22. The composition, according to claim 1, further comprising at least two active ingredients.

23. A method of delivering a cosmetic agent or pharmaceutical agent epidermis tissue of a human or animal which comprises topically applying to the skin of the human or animal a composition according to claim 4.

24. A method for treating a patient suffering from onychomycosis which comprises topically applying to the patient's nail(s) infected with fungus a composition according to claim 11.

25. A method of treating a patient suffering from onychomycosis which comprises topically applying to the patient's nail(s) infected with fungus a composition according to claim 12.

26. A method of making a composition suitable for cutaneous delivery of at least one cosmetic agent or a pharmaceutical agent or both wherein said composition comprises at least one cosmetic agent or a pharmaceutical agent or both, two biocompatible organic solvents 6 to 30% by weight of lecithin, 0.5 to 19% by weight of at least one or more surfactant, wherein said surfactant comprises a docusate, 40 to 65% by weight water, 1 to 15% by weight of urea and 0.5 to 5% by weight of a thickener; wherein the organic solvents comprise 2 to 30% of isopropyl myristate and 0.5 to 20% of propylene glycol; and which method comprises:
  a. dissolving 6 to 30% by weight of lecithin, in at least two biocompatible organic solvents comprising isopropyl myristate and propylene glycol;
  b. adding 0.5 to 19% by weight of one or more surfactants to the composition of step (a); wherein said one or more surfactants comprises a docusate;
  c. dissolving a cosmetic agent or pharmaceutically active compound or both in the solvent-polar lipid, surfactant mixture of step (b);
  d. adding 1 to 15% by weight of urea and 0.5 to 5% by weight of thickener(s) to water; and
  e. combining the composition from c and d and optionally adjusting the pH to about 5.5 to about 7.5.

27. A composition prepared according to the method of claim 26.

28. A method of making a composition suitable for cutaneous delivery of at least one cosmetic agent or a pharmaceutical agent or both wherein said composition comprises at least one cosmetic agent or a pharmaceutical agent or both, two biocompatible organic solvents, 6 to 30% by weight of lecithin, 0.5 to 19% by weight of at least one or more surfactant, wherein said surfactant comprises a docusate, 40 to about 65% by weight water, 1 to 15% by weight of urea and 0.5 to 5% by weight of a thickener; wherein the organic solvents comprise 2 to 30% of isopropyl myristate and 0.5 to 20% of propylene glycol; and which method comprises:
  a. dissolving 6 to 30% by weight of lecithin, in at least two biocompatible organic solvents comprising isopropyl myristate and propylene glycol;
  b. adding 0.5 to 19% by weight of one or more surfactants to the composition of step (a); wherein said one or more surfactants comprises a docusate;
  c. adding 1 to 15% by weight of urea and 0.5 to 5% by weight of thickener(s) to water;
  d. dissolving a cosmetic agent or pharmaceutically active compound or both in the thickened aqueous urea; and
  e. combining the composition from (b) and (d) and optionally adjusting the pH to about 5.5 to about 7.5.

29. A composition prepared according to the method of claim 28.

30. A method for treating a patient suffering from nail psoriasis which comprises topically applying to the patient's nail(s) a composition according to claim 19.

31. A method for treating a patient suffering from nail psoriasis which comprises topically applying to the patient's nail(s) a composition according to claim 21.

32. A method for treating a patient for infections which comprises topically applying to the patient a composition according to claim 1 that further comprises an effective amount of an antibacterial agent.

33. The method of claim 28, wherein said at least one surfactant is selected from the group consisting of docusate sodium, docusate sodium benzoate, and docusate calcium, the thickener is selected from the group of polyethylene glycol, methyl cellulose, and carbomer.

34. The method of claim 26, wherein said at least one surfactant is selected from the group consisting of docusate sodium, docusate sodium benzoate, and docusate calcium, the thickener is selected from the group of polyethylene glycol, methyl cellulose, and carbomer.

\* \* \* \* \*